US012635954B2

(12) United States Patent
Zhang et al.

(10) Patent No.: US 12,635,954 B2
(45) Date of Patent: May 26, 2026

(54) USER FEATURE VALUE MEASUREMENT METHOD AND APPARATUS, STORAGE MEDIUM AND ELECTRONIC DEVICE

(71) Applicant: BOE TECHNOLOGY GROUP CO., LTD., Beijing (CN)

(72) Inventors: Xun Zhang, Beijing (CN); Xiaoran Sun, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1079 days.

(21) Appl. No.: 17/768,495

(22) PCT Filed: May 20, 2021

(86) PCT No.: PCT/CN2021/094904
§ 371 (c)(1),
(2) Date: Apr. 13, 2022

(87) PCT Pub. No.: WO2021/258937
PCT Pub. Date: Dec. 30, 2021

(65) Prior Publication Data
US 2024/0298973 A1 Sep. 12, 2024

(30) Foreign Application Priority Data

Jun. 24, 2020 (CN) .......................... 202010589867.0

(51) Int. Cl.
*A61B 5/00* (2006.01)
*G16H 50/70* (2018.01)
*A61B 5/145* (2006.01)

(52) U.S. Cl.
CPC .......... *A61B 5/7267* (2013.01); *A61B 5/7246* (2013.01); *G16H 50/70* (2018.01); *A61B 5/14532* (2013.01)

(58) Field of Classification Search
CPC . A61B 5/7267; A61B 5/7246; A61B 5/14532; G16H 50/70
See application file for complete search history.

(56) References Cited

U.S. PATENT DOCUMENTS 8,366,627 B2   2/2013   Kashif et al.
8,821,402 B2   9/2014   Kashif et al.
(Continued)

FOREIGN PATENT DOCUMENTS

CN       101627905 A       1/2010
CN       101627905 B       8/2011
(Continued)

OTHER PUBLICATIONS

Office action from Chinese Application No. 202010589867.0 dated Aug. 22, 2022.
(Continued)

*Primary Examiner* — David E Choi
(74) *Attorney, Agent, or Firm* — Calfee, Halter & Griswold LLP

(57) ABSTRACT

A user feature value measurement method includes: generating training data of at least one user that by acquiring standard feature values and measurement feature data input multiple times by the user, wherein the training data of each user comprises a standard feature value set and a measurement feature data set; training a data calculation model of each user based on the training data; acquiring current feature data of a target user, and determining a data calculation model of the target user according to the current feature data and the measurement feature data set; and calculating a user feature value of the target user based on the current feature data and the data calculation model of the target user.

15 Claims, 3 Drawing Sheets

(56) References Cited

U.S. PATENT DOCUMENTS

| | | | | |
|---|---|---|---|---|
| 11,250,951 | B2* | 2/2022 | Takata | G16H 50/70 |
| 11,810,671 | B2* | 11/2023 | Leventhal | A61B 5/7278 |
| 12,080,052 | B2* | 9/2024 | Hu | G06T 7/0016 |
| 12,394,524 | B2* | 8/2025 | Ng | G06N 3/08 |
| 2006/0002600 | A1* | 1/2006 | Martel-Pelletier | A61B 5/055 |
| | | | | 382/128 |
| 2010/0063405 | A1 | 3/2010 | Kashif et al. | |
| 2013/0204139 | A1 | 8/2013 | Kashif et al. | |
| 2014/0279746 | A1* | 9/2014 | De Bruin | G16H 50/70 |
| | | | | 706/46 |
| 2014/0357965 | A1 | 12/2014 | Kashif et al. | |
| 2015/0133798 | A1 | 5/2015 | Hu | |
| 2016/0374624 | A1 | 12/2016 | Hu | |
| 2017/0358093 | A1 | 12/2017 | Baltsen | |
| 2018/0260954 | A1* | 9/2018 | Jung | G06F 18/2413 |
| 2019/0180882 | A1* | 6/2019 | Han | G16H 50/30 |
| 2020/0251182 | A1* | 8/2020 | Platt | G16B 30/10 |
| 2021/0241916 | A1* | 8/2021 | Wexler | A61B 5/6802 |
| 2021/0244318 | A1* | 8/2021 | Sashen | A61B 5/1123 |
| 2021/0257067 | A1* | 8/2021 | Yabuuchi | G06N 5/04 |
| 2022/0076834 | A1* | 3/2022 | Hanlon, Jr. | G16H 50/20 |
| 2022/0376994 | A1* | 11/2022 | Mishra | G06N 3/096 |

| | | | | |
|---|---|---|---|---|
| 2024/0298973 | A1* | 9/2024 | Zhang | A61B 5/7267 |
| 2025/0037863 | A1* | 1/2025 | Kitade | A61B 5/00 |
| 2025/0166818 | A1* | 5/2025 | Ruby | G16H 40/20 |

FOREIGN PATENT DOCUMENTS

| | | |
|---|---|---|
| CN | 102429651 A | 5/2012 |
| CN | 102429651 B | 10/2013 |
| CN | 103610456 A | 3/2014 |
| CN | 103654760 A | 3/2014 |
| CN | 103610456 B | 6/2015 |
| CN | 103654760 B | 8/2016 |
| CN | 106650784 A | 5/2017 |
| CN | 108197664 A | 6/2018 |
| CN | 108498089 A | 9/2018 |
| CN | 109758160 A | 5/2019 |
| CN | 109840588 A | 6/2019 |
| CN | 110705598 A | 1/2020 |
| WO | 2010030612 A1 | 3/2010 |

OTHER PUBLICATIONS

International Search Report from PCT/CN2021/094904 dated Aug. 18, 2022.
Written Opinion from PCT/CN2021/094904 dated Aug. 18, 2022.

* cited by examiner

USER FEATURE VALUE MEASUREMENT METHOD AND APPARATUS, STORAGE MEDIUM AND ELECTRONIC DEVICE

CROSS-REFERENCE TO RELATED APPLICATIONS

The disclosure is the U.S. national phase application of PCT Application No. PCT/CN2021/094904, filed May 20, 2021, which claims the priority of the Chinese Patent Application No. 202010589867.0, filed on Jun. 24, 2020, and the titled "USER FEATURE VALUE MEASURE-MENT METHOD AND APPARATUS, STORAGE MEDIUM AND ELECTRONIC DEVICE", the entire contents of both of which are hereby incorporated by reference in its entirety.

TECHNICAL FIELD

The disclosure relates to the technical field of information measurement, and in particular, to a user feature value measurement method and apparatus, a computer-readable storage medium, and an electronic device.

BACKGROUND

Diabetes is an important cause of death, disease burden, and medical and health economic burden. Blood glucose management is a key factor in diabetes management, and blood glucose measurement is the key to blood glucose management. Therefore, non-invasive blood glucose measurement technology has become more important.

In the non-invasive blood glucose measurement method in the prior art, one device is only allowed to be used by one user, resulting in a relatively high measurement cost.

Therefore, it is necessary to design a new user feature value measurement method.

It should be noted that the information disclosed in the background section above is only used to enhance the understanding of the background of the disclosure, and therefore may include information that does not constitute the prior art known to those of ordinary skill in the art.

SUMMARY

According to a first aspect of the disclosure, there is provided a user feature value measurement apparatus, including:

an acquisition module, configured to generate training data of at least one user by acquiring standard feature values and measurement feature data input multiple times by the user, wherein the training data of each user includes a standard feature value set and a measure-ment feature data set;

a training module, configured to train a data calculation model of each user based on the training data;

a matching module, configured to acquire current feature data of a target user, and determine a data calculation model of the target user according to the current feature data and the measurement feature data set; and a calculation module, configured to calculate a user fea-ture value of the target user based on the current feature data and the data calculation model of the target user.

In some embodiments of the disclosure, the apparatus further includes:

a judgment module, configured to acquire a current stan-dard feature value of the target user when the user feature value is not within a preset range; and a first updating module, configured to update the training data based on the current feature data and the current standard feature value when a difference between the user feature value and the current standard feature value is greater than a preset value.

In some embodiments of the disclosure, the apparatus further includes:

a measurement module, configured to acquire a current standard feature value of the target user at a preset time interval; and a second updating module, configured to update the training data based on the current feature data and the current standard feature value when a difference between the user feature value and the current standard feature value is greater than a preset value.

In some embodiments of the disclosure, the updating the training data based on the current feature data and the current standard feature value includes:

determining a target correlation degree as a maximum value of correlation degrees calculated between the current feature data of the target user and a plurality of measurement feature data corresponding to the target user;

replacing the measurement feature data corresponding to the current feature data by the current feature data when the target correlation degree is greater than or equal to a first preset threshold; and replacing the standard feature values corresponding to the current feature data by the current standard feature value.

In some embodiments of the disclosure, the updating the training data based on the current feature data and the current standard feature value further includes:

when the target correlation degree is less than the first preset threshold, adding the current feature data and the current standard feature value to the training data, and deleting a group of standard feature values and mea-surement feature data firstly input by the target user.

In some embodiments of the disclosure, the training the data calculation model of the user based on the training data includes:

updating parameters in the data calculation model based on the training data.

In some embodiments of the disclosure, the acquiring the current feature data of the target user and determining the data calculation model according to the current feature data and the measurement feature data includes:

measuring the current feature data of the target user, and calculating correlation coefficients between the current feature data and multiple measurement feature data sets; and determining a data calculation model corresponding to measurement feature data with a correlation coefficient greater than or equal to a second preset threshold as the data calculation model of the target user.

In some embodiments of the disclosure, the calculating the correlation coefficients between the current feature data and the multiple measurement feature data sets includes:

obtaining a correlation coefficient by calculating an aver-age value of correlation degrees between the current feature data and each measurement feature data in one of the multiple measurement feature data sets; and obtaining the correlation coefficients by traversing the multiple measurement feature data sets.

According to an aspect of the disclosure, there is provided a user feature value measurement method, including:

generating training data of at least one user by acquiring standard feature values and measurement feature data input multiple times by the user, wherein the training data of each user includes a standard feature value set and a measurement feature data set;

training a data calculation model of each user based on the training data;

acquiring current feature data of a target user, and determining a data calculation model of the target user according to the current feature data and the measurement feature data set; and calculating a user feature value of the target user based on the current feature data and the data calculation model of the target user.

In some embodiments of the disclosure, the method further includes:

acquiring a current standard feature value of the target user when the user feature value is not within a preset range; and updating the training data based on the current feature data and the current standard feature value when a difference between the user feature value and the current standard feature value is greater than a preset value.

In some embodiments of the disclosure, the method further includes:

acquiring a current standard feature value of the target user at a preset time interval; and updating the training data based on the current feature data and the current standard feature value when a difference between the user feature value and the current standard feature value is greater than a preset value.

In some embodiments of the disclosure, the updating the training data based on the current feature data and the current standard feature value includes:

determining a target correlation degree as a maximum value of correlation degrees calculated between the current feature data of the target user and a plurality of measurement feature data corresponding to the target user;

replacing the measurement feature data corresponding to the current feature data by the current feature data when the target correlation degree is greater than or equal to a first preset threshold; and replacing the standard feature values corresponding to the current feature data by the current standard feature value.

In some embodiments of the disclosure, the updating the training data based on the current feature data and the current standard feature value further includes:

when the target correlation degree is less than the first preset threshold;

adding the current feature data and the current standard feature value to the training data, and deleting a group of standard feature values and measurement feature data firstly input by the target user.

In some embodiments of the disclosure, the training the data calculation model of the user based on the training data includes:

updating parameters in the data calculation model based on the training data.

In some embodiments of the disclosure, the acquiring the current feature data of the target user and determining the data calculation model according to the current feature data and the measurement feature data includes:

measuring the current feature data of the target user, and calculating correlation coefficients between the current feature data and multiple measurement feature data sets; and determining a data calculation model corresponding to measurement feature data with a correlation coefficient greater than or equal to a second preset threshold as the data calculation model of the target user.

In some embodiments of the disclosure, the calculating the correlation coefficients between the current feature data and the multiple measurement feature data sets includes:

obtaining a correlation coefficient by calculating an average value of correlation degrees between the current feature data and each measurement feature data in one of the multiple measurement feature data sets; and obtaining the correlation coefficients by traversing the multiple measurement feature data sets.

According to an aspect of the disclosure, there is provided a computer-readable storage medium on which a computer program is stored, wherein the program, when executed by a processor, is used for implementing the user feature value measurement method according to any one of the above items.

According to an aspect of the disclosure, there is provided an electronic device, including:

processors; and a memory, configured to store one or more programs which, when executed by one or more of the processors, cause the one or more of the processors to implement the user feature value measurement method according to any one of the above items.

It should be understood that the above general description and the following detailed description are only exemplary and explanatory, and cannot limit the disclosure.

BRIEF DESCRIPTION OF THE DRAWINGS

The drawings herein, which are incorporated in and constitute a part of the specification, illustrate embodiments consistent with the disclosure, and serve to explain the principles of the disclosure together with the description. Obviously, the drawings in the following description are only some embodiments of the disclosure. For those of ordinary skill in the art, other drawings may be obtained based on these drawings without creative efforts. In the attached drawings.

DETAILED DESCRIPTION

Figure 1:
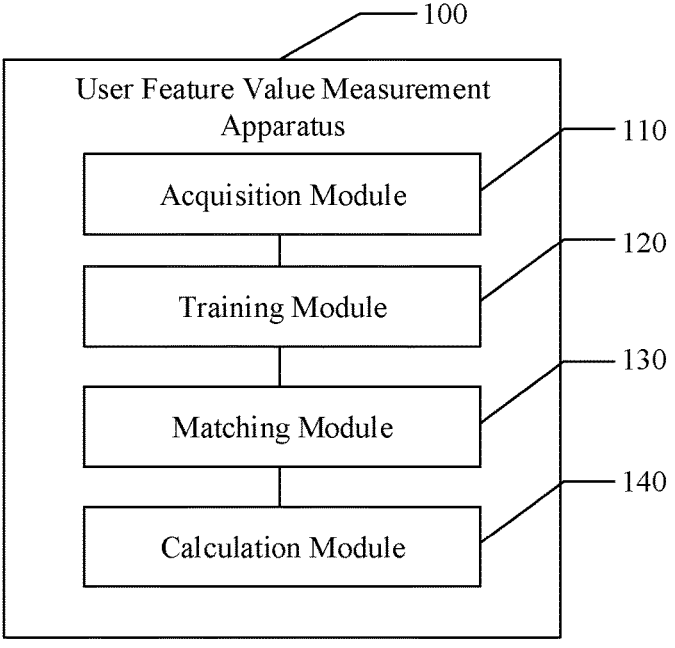
FIG. 1 schematically shows a schematic composition diagram of a user feature value measurement apparatus according to some embodiments of the disclosure.

Example embodiments will now be described more fully with reference to the accompanying drawings. Example embodiments, however, can be embodied in various forms and should not be construed as limited to the examples set forth herein; rather, these embodiments are provided so that this disclosure will be thorough and complete, and will fully convey the concept of example embodiments to those skilled in the art. The described features, structures, or characteristics may be combined in any suitable manner in one or more embodiments.

Furthermore, the drawings are merely schematic illustrations of the disclosure and are not necessarily drawn to scale. The same reference numerals in the drawings denote the same or similar parts, and thus repeated descriptions thereof will be omitted. Some of the block diagrams shown in the drawings are functional entities that do not necessarily correspond to physically or logically separate entities. These functional entities may be implemented in software, or in one or more hardware modules or integrated circuits, or in different networks and/or processor devices and/or microcontroller devices.

Diabetes is an important cause of death, disease burden and medical and health economic burden. Our country has the largest number of diabetes patients in the world. There is currently no cure for diabetes, and once the disease occurs, lifelong treatment is required, and there are many complications and high treatment costs. In order to improve the quality of life of diabetic patients and prolong their survival time, it is necessary to provide long-term and in-depth support and intervention for patients.

Wherein blood sugar management is a key factor in diabetes management. The main factors that affect blood sugar are eating habits, exercise patterns, drug use, and insulin secretion levels. In blood glucose measurement devices in the related art, only a near-infrared-based photoplethysmography measurement technology truly realizes a non-invasive blood glucose measurement. Before the official test, it takes a long period of time to train a data calculation model built into an invasive measurement training device. Once the model is mature, the device can only measure the blood sugar of a single subject, and it needs to be repeatedly calibrated after a period of time. The cost of such a device is high due to integration considerations.

In some embodiments, based on the above shortcomings, the disclosure first provides a user feature value measurement apparatus, which may be applied to measure user feature values, for example, measuring the user's blood sugar, blood pressure, and the like. Referring to FIG. 1, the user feature value measurement apparatus 100 includes: an acquisition module 110, a training module 120, a matching module 130, and a calculation module 140.

Wherein the acquisition module 110 may be configured to acquire training data of a user that is constituted by standard feature values and measurement feature data input multiple times by at least one user, wherein the training data of each user includes a standard feature value set and a measurement feature data set; the training module 120 may be configured to train a data calculation model of each user by using the training data; the matching module 130 may be configured to acquire current feature data of a target user, and determine a data calculation model of the target user according to the current feature data and the measurement feature data set; and the calculation module 140 may be configured to calculate a user feature value of the target user by using the current feature data and the data calculation model of the target user.

According to the user feature value measurement apparatus provided in some embodiments, compared with the prior art, on the one hand, the training data of a plurality of users may be input, and the training of the calculation model of the plurality of users may be completed, so that the apparatus may be used by the plurality of users, which saves the cost of measurement; on the other hand, the user's current feature data may be used to complete the login and the data calculation model of the target user may be obtained to complete the calculation, without the need to develop other login programs again, thereby saving computing resources. At the same time, the user can directly obtain the data calculation model corresponding to the user without tedious login to complete the acquisition of the user feature value, which enhances the user experience and speeds up the measurement efficiency.

Hereinafter, various modules of the user feature value measurement apparatus in some embodiments will be described in more detail with reference to the accompanying drawings and embodiments.

The obtaining module 110 may be configured to acquire training data of a user that is constituted by standard feature values and measurement feature data input multiple times by at least one user.

In some embodiments of the disclosure, the standard feature values may be blood glucose values, blood pressure values, blood lipid values, etc., which are not specifically limited in this exemplary embodiment.

The following is a detailed description by taking the above standard feature values as the blood glucose values as an example.

In some embodiments of the disclosure, the non-invasive blood glucose measurement may be blood glucose measurement based on photoplethysmography (PPG). Fingertips may be illuminated by a plurality of LEDs, an optical signal absorbed by tissue may be collected by photoelectric sensors, and the waveform is shown as FIG. 2. Signal features are extracted, and the blood glucose values are calculated based on the Lambert-Beer law.

Based on the Lambert-Beer law, the absorbance may be expressed as the following formula:

$$A^{\lambda_i} = \ln\frac{I_0^{\lambda_i}}{I^{\lambda_i}} = DPF \times \rho \sum \varepsilon_i^{\lambda_i} C_i + G$$

wherein DPF is a differential path factor, p is a horizontal distance from a light source to a receiver, G is background absorption, $$\varepsilon_i^{\lambda_i}$$

represents the molar absorption coefficient, $$I_0^{\lambda_i}$$

represents the incident light intensity at the wavelength $\lambda_i$, and $C_i$ may represent the concentration of light absorbing substances.

Figure 2:
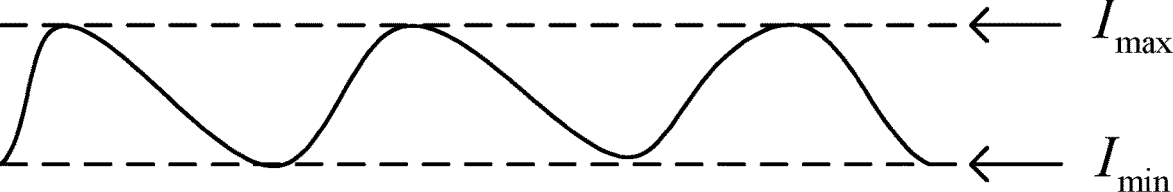
FIG. 2 schematically shows a schematic diagram of PPG signal waveform analysis according to some embodiments of the disclosure.

In the case of only one photoelectric sensor receiver, the AC/DC relationship of the PPG signal is fully considered, and the PPG signal measured by the receiver has a maximum value $I_{max}$ and a minimum value $I_{min}$ under the illumination of the incident light with a fixed wavelength, as shown in FIG. 2. The main reason for the generation of the AC portion is the absorption of light by an arterial pulsation portion, and $\partial A^{\lambda_i}$ is analyzed herein, that is:

$$\partial A^{\lambda_i} = A_{max}^{\lambda_i} - A_{min}^{\lambda_i} = \ln\frac{I_0^{\lambda_i}}{I_{max}^{\lambda_i}} - \ln\frac{I_0^{\lambda_i}}{I_{mim}^{\lambda_i}} = \ln\frac{I_{min}^{\lambda_i}}{I_{max}^{\lambda_i}}$$

wherein $$I_{max}^{\lambda_i}$$

and $$I_{min}^{\lambda_i}$$

respectively represent the maximum light intensity and the minimum light intensity measured by the sensor at the wavelength $\lambda_i$. $\partial A^{\lambda_i}$ may be equivalent to the model under the incident light intensity $$I_{max}^{\lambda_i}$$

and the corresponding emergent light intensity $$I_{min}^{\lambda_i},$$

that is, the partial absorbance $\partial A^{\lambda_i}$ generated by the arterial pulsation.

By selecting the appropriate light source wavelength, the main light-absorbing substances are blood glucose and functional hemoglobin (oxyhemoglobin and/or reduced hemoglobin), and then the blood glucose concentration $C_{glucose}$ may be calculated by establishing a multi-channel equation. That is, the data calculation model applied to blood glucose measurement is as follows:

$$C_{glucose} =$$

$$F(\partial A^{\lambda_1}, \partial A^{\lambda_2}, \ldots, \partial A^{\lambda_L}) = \alpha_1 \cdot \partial A^{\lambda_1} + \alpha_2 \cdot \partial A^{\lambda_2} + \ldots + \alpha_L \cdot \partial A^{\lambda_L} + \beta$$

wherein $\alpha_1, \ldots, \alpha_L, \beta$ are fixed values, which are related to the physiological environment of the user's measurement location. Therefore, it is necessary to collect the invasive blood glucose values before use, that is, $\partial A^{\lambda_1}, \partial A^{\lambda_2}, \ldots, \partial A^{\lambda_L}$ of the standard feature values and the measurement feature data, the parameters $\alpha_1, \ldots, \alpha_L, \beta$ in the data calculation model may be inversely deduced, and then the data calculation model after training is used to calculate the blood glucose values. Because the receiver needs to complete the sensing of multi-channel light, it needs to have a wide acceptance range, high resolution, and high hardware cost, and the data processing and storage mode in the related art makes a single device only support one person, resulting in high measurement cost.

In some embodiments, the training data that is constituted by the standard feature values and the measurement feature data input multiple times by the at least one user may be obtained to form the training data. That is, each user needs to input the standard feature values and the measurement feature data corresponding to the standard feature values multiple times, and the training data of each user includes the standard feature value set and the measurement feature data set, wherein the standard feature value set includes a plurality of standard feature values, and the measurement feature data set includes the same number of the measurement feature data as the standard feature values, and wherein the measurement feature data and standard feature values are in one-to-one correspondence.

Specifically, taking the measurement of the blood glucose as an example for detailed description, the invasive blood glucose values $C_{T_i}$ (i.e., the standard feature values) and the corresponding non-invasive measurement feature values (i.e., the above measurement feature data [$\partial A^{\lambda_1}, \partial A^{\lambda_2}, \ldots, \partial A^{\lambda_L}$]) may be input by each user multiple times, and a training dataset $\psi=[\varphi_1, \varphi_2, \ldots, \varphi_N]$ is formed, wherein $$\varphi_i = \left[\partial A_i^{\lambda_1}, \partial A_i^{\lambda_2}, \ldots, \partial A_i^{\lambda_L}, C_{T_i}\right]^T,$$

and $C_{T_i}$ represents the invasive measurement blood glucose values (i.e., the standard feature values), and wherein L and N are both positive integers.

The training module 120 may be configured to train a data calculation model of each user by using the training data.

In some embodiments of the disclosure, the above data calculation model may be trained by using the above obtained training data, wherein the training data calculation model is as follows:

$$C_{glucose} =$$

$$F(\partial A^{\lambda_1}, \partial A^{\lambda_2}, \ldots, \partial A^{\lambda_L}) = \alpha_1 \cdot \partial A^{\lambda_1} + \alpha_2 \cdot \partial A^{\lambda_2} + \ldots + \alpha_L \cdot \partial A^{\lambda_L} + \beta$$

wherein, $\alpha_1, \ldots, \alpha_L, \beta$ are fixed values, which are related to the physiological environment of the user's measurement location; when training the above data calculation model, the parameters (i.e., $\alpha_1, \ldots, \alpha_L, \beta$) in the data calculation model may be inversely deduced by using $\partial A^{\lambda_1}, \partial A^{\lambda_2}, \ldots, \partial A^{\lambda_L}$ of the collected invasive blood glucose values (i.e., the standard feature values) and the measurement feature data, and the parameters in the original data calculation model are replaced by the deduced parameters to complete the training of the above data calculation model.

In some embodiments, each user corresponds to one data calculation model, that is, when the data calculation model is trained as described above, the training data of each user is used to train the data calculation model corresponding to the user, and the corresponding relationship between each data calculation model and the user is determined.

In some embodiments, after completing the training of the user's data calculation model, a data file corresponding to each user may be generated, and the data file may include the training data y' and a feature value prediction set $$\Theta = [\theta_1, \theta_2, \dots, \theta_M], \text{ wherein } \theta_j = \left[\partial A_j^{\lambda_1}, \partial A_j^{\lambda_2}, \dots, \partial A_j^{\lambda_L}, C_{C_j}\right]^T,$$

and wherein $C_{C_j}$ represents the measurement feature values, and M is a positive integer.

The matching module 130 may be configured to acquire current feature data of a target user, and determine a data calculation model of the target user according to the current feature data and the measurement feature data set.

In some embodiments of the disclosure, the current feature data of the target user may be measured first, which may be specifically $[\partial A^{\lambda_1}, \partial A^{\lambda_2}, \dots, \partial A^{\lambda_L}]^T$, the correlation coefficients between the current feature data and multiple measurement feature data sets may be calculated respectively. Specifically, the correlation degrees between the current feature data and each measurement feature data in one of the measurement feature data sets are calculated respectively, and an average value of a plurality of correlation degrees is calculated to obtain the correlation coefficient.

In some embodiments, a correlation analysis is respectively performed on the previous L rows of the training data $\Psi$ of all the users by using the current feature data $[\partial A^{\lambda_1}, \partial A^{\lambda_2}, \dots, \partial A^{\lambda_L}]^T$, that is, the correlation coefficient is obtained by performing the correlation analysis with the measurement feature data. That is to say, the correlation degrees between the current feature data and the multiple measurement feature data sets of the users are calculated, and the average value is calculated to obtain the correlation coefficient. When the above correlation coefficient is greater than or equal to a second preset threshold, it is determined that the user is logged in. That is, the data calculation model corresponding to the measurement feature data with the correlation coefficient greater than or equal to the second preset threshold is determined as the data calculation model of the target user. In other words, the values of $\alpha_1, \dots, \alpha_L$, $\beta$ in the data calculation model of the target user are determined.

The calculation module 140 may be configured to calculate a user feature value of the target user by using the current feature data and the data calculation model of the target user.

In some embodiments of the disclosure, the user feature value of the target user may be obtained by substituting the current measurement data of the target user into the data calculation model determined by the above matching module 130.

In some embodiments, the user feature value and the current feature data may be stored to provide comparison for subsequent measurement, or when the user's subsequent feature data is the same as the current measurement data, they may be directly retrieved and used without the need to repeat the calculation process.

In some embodiments of the disclosure, the user feature value measurement apparatus according to the disclosure may further include a judgment module and a first update module, and the judgment module is configured to judge whether the user feature value is within a preset range, wherein the preset range may be determined according to the specific form of the user feature value and the user's physical condition are customized. For example, when the user feature value is the user's blood glucose value, the preset range may be greater than or equal to 3.9 mmol/L and less than or equal to 6.1 mmol/L, that is, there is a risk when the user's blood glucose value is too high or too low; and in some embodiments, the above preset range is not specifically limited.

Figure 3:
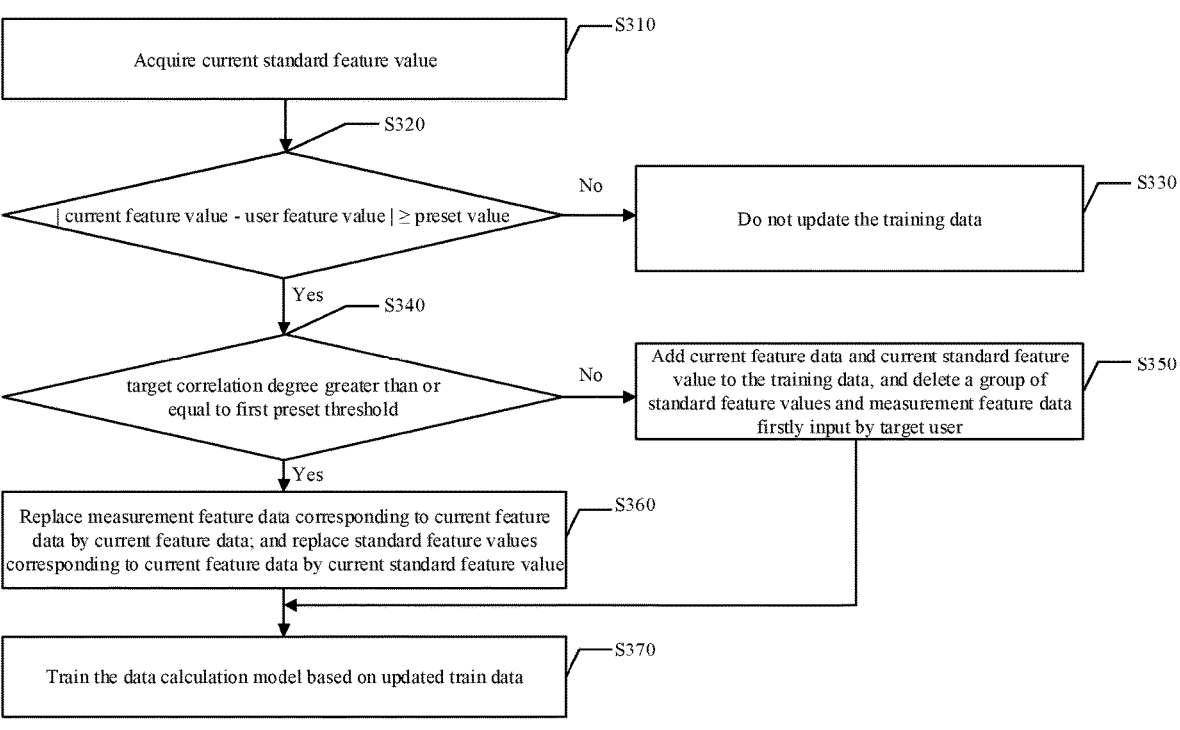
FIG. 3 schematically shows a flowchart of updating training data according to some embodiments of the disclosure.

When the feature value of the target user is not in the above preset range, referring to FIG. 3, step S310 may be performed first to acquire a current standard feature value, specifically, the current standard feature value of the target user is first acquired, and then step S320 is performed to determine the size of the difference between the current standard feature value and the user feature value. If the absolute value of the difference value is greater than or equal to the preset value, then steps S340 to S370 are performed: the training data is updated by using the current feature data and the current standard feature value, and the data calculation model of the target user is retrained. If the absolute value of the difference is smaller than the preset value, step S330 is executed: it is determined that the measurement of user feature value is accurate, and the training data does not need to be updated.

In some embodiments, when the user feature value is the user's blood glucose value, and when it is necessary to obtain the standard feature value of the target user, step S340 may be executed. The absolute value of the difference between the user feature value and the standard feature value (that is, the absolute value of the difference between the non-invasive blood glucose value collected by using the apparatus according to the present solution and the blood glucose value measured by the invasive measurement) may be judged, and the size of the absolute value and the preset value may be judged. The preset value may be 1 mmol/L, 2 mmol/L, etc., and it may also be customized according to requirements, which is not specifically limited in this exemplary embodiment. In another exemplary embodiment, the above determined feature value prediction set may also be used to make judgment. First, the feature value prediction set unit $$\theta_Q = \left[\partial A_Q^{\lambda_1}, \partial A_Q^{\lambda_2}, \dots, \partial A_Q^{\lambda_L}, C_{C_Q}\right]^T$$

of the target user may be marked, wherein Q is greater than or equal to 1 and less than or equal to M, and the invasive measurement result is recorded, that is, the current standard feature value $C_{T_Q}$. If $|C_{T_Q} - C_{C_Q}| > 1$ mmol/L, it is considered that the subject's physiological environment has changed, and the training data and the data calculation model need to be updated, otherwise the error is considered acceptable, and the data calculation model of the target user does not need to be retrained.

In another exemplary implementation of the disclosure, a preset time may be set, and the current annotation feature values of the user may be obtained at intervals of the preset time. After the standard feature values are obtained, the absolute value of the difference between the user feature value and the standard feature value (that is, the absolute value of the difference between the non-invasive blood glucose value collected by using the apparatus according to the present solution and the blood glucose value measured by the invasive measurement) may be judged, and the size of the absolute value and the preset value may be judged. The preset value may be 1 mmol/L, 2 mmol/L, etc., and it may also be customized according to requirements, which is not specifically limited in this exemplary embodiment; and the preset time may be 5 days, 6 days, etc., which may be customized according to different users and not specifically limited in this exemplary embodiment. In another exemplary embodiment, the above determined feature value prediction set may also be used to make judgment. First, the feature value prediction set unit $$\theta_Q = \left[ \partial A_Q^{\lambda_1}, \partial A_Q^{\lambda_2}, \ldots, \partial A_Q^{\lambda_L}, C_{C_Q} \right]^T$$

of the target user may be marked, and the invasive measurement result is recorded, that is, the current standard feature value $C_{T_Q}$. If $|C_{T_Q} - C_{C_Q}| > 1$ mmol/L, it is considered that the subject's physiological environment has changed, and the training data and the data calculation model need to be updated, otherwise the error is considered acceptable, and the data calculation model of the target user does not need to be retrained.

In some embodiments of the disclosure, when the training data of the data model needs to be updated, correlation degrees between the current feature data of the target and a plurality of measurement feature data in the training data of the user may be firstly determined, and then a maximum value among the multiple correlation degrees is used as a target correlation degree, and then step S340 is performed to determine the magnitude relationship between the target correlation degree and a first preset threshold. If the target correlation degree is greater than or equal to the first preset threshold, step S360 is performed: the measurement feature data matching with the current feature data is replaced by the current feature data, and the standard feature values matching with the current feature data are replaced by the current standard feature value. If the target correlation degree is less than or equal to the first preset threshold, step S350 is executed, the current feature data and the current standard feature value are added to the training data, and a group of standard feature values and measurement feature data firstly input by the target user are deleted, Finally, step S370 is executed, the training data is used to retrain the data calculation model after the update.

In some embodiments, the first preset threshold may be 0.8, or may be 0.9, 0.85, etc., which is not specifically limited in this exemplary embodiment.

Specifically, first, it may be determined whether a non-invasive measurement parameter vector, that is, the current feature data $$\xi_Q = \left[ \partial A_Q^{\lambda_1}, \partial A_Q^{\lambda_2}, \ldots, \partial A_Q^{\lambda_L} \right],$$

has measurement feature data whose correlation degree is greater than or equal to the first preset threshold in the existing training data. If the correlation degree between the measurement feature data $$\xi_P = \left[ \partial A_P^{\lambda_1}, \partial A_P^{\lambda_2}, \ldots, \partial A_P^{\lambda_L} \right]$$

and the current feature data is greater than or equal to 0.8 in the training data $\Psi$, $\varphi_P$ is replaced by $$\varphi_Q = \left[ \partial A_Q^{\lambda_1}, \partial A_Q^{\lambda_2}, \ldots, \partial A_Q^{\lambda_L}, C_{T_Q} \right]^T;$$

and if there is no $\varphi_P$, the first measurement feature data $\varphi_1$ of the training data $\Psi$ is removed according to the input time, the remaining measurement feature data is shifted to the left, and $\varphi_N$ is replaced by the current feature data $\varphi_Q$ into the training data, and then the new training data is used to train the data calculation model of the target user.

Figure 4:
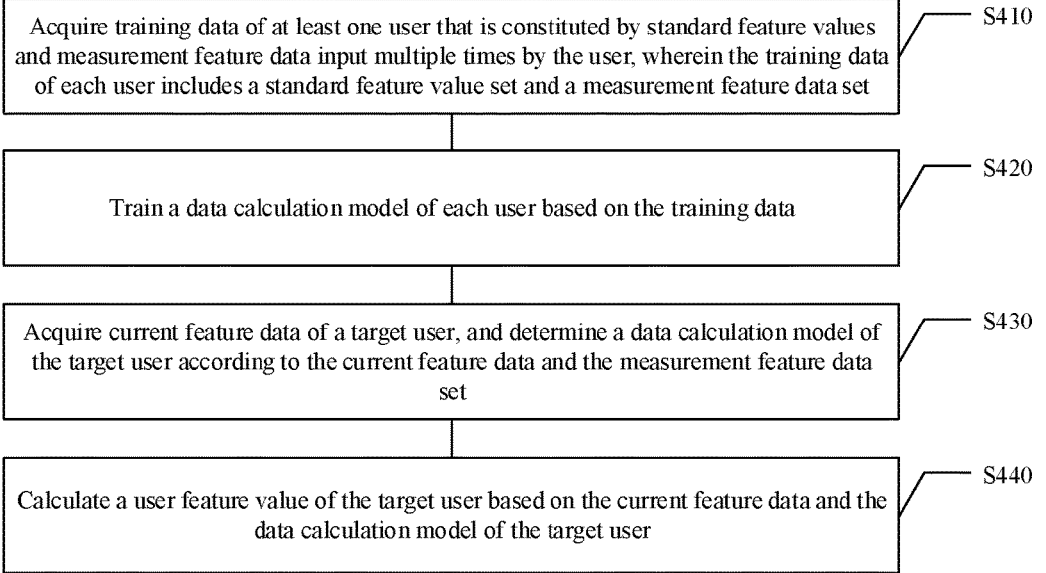
FIG. 4 schematically shows a flowchart of a user feature value measurement method according to some embodiments of the disclosure.

The disclosure further provides a new user feature value measurement, referring to FIG. 4, the above user feature value measurement method may include the following steps:

S410, acquiring feature information of users within a scope of an event occurrence area;

S420, using the user who is adapted to the event as a target user according to the feature information;

S430, determining an association relationship between the target user and each of event participants, and calculating the weight of the target user of each of the event participants according to the association relationship; and

S440, determining a video to be played in the event occurrence area according to the weight.

Since various functional modules of the user feature value measurement apparatus according to the exemplary embodiments of the disclosure correspond to the steps of the above exemplary embodiments of the user feature value measurement method, please refer to the above embodiments of the user feature value measurement method according to the disclosure for details not disclosed in the embodiments of the method of the disclosure.

It should be noted that although several modules or units of the apparatus for action performance are mentioned in the above detailed description, this division is not mandatory. Indeed, according to embodiments of the disclosure, the features and functions of two or more modules or units described above may be embodied in one module or unit. Conversely, the features and functions of one module or unit described above may be further divided into multiple modules or units to be embodied.

In addition, in some embodiments of the disclosure, an electronic device capable of realizing the above user feature value measurement is further provided.

As will be appreciated by one skilled in the art, various aspects of the disclosure may be implemented as a system, method or program product. Therefore, various aspects of the disclosure may be embodied in the following forms: a complete hardware embodiment, a complete software embodiment (including firmware, microcode, etc.), or a combination of hardware and software aspects, which may be collectively referred to herein as a "circuit", "module" or "system".

An electronic device 500 according to such an embodiment of the disclosure is described below with reference to FIG. 5. The electronic device 500 shown in FIG. 5 is only an example, and should not impose any limitation on the functions and scope of use of the embodiments of the disclosure.

Figure 5:
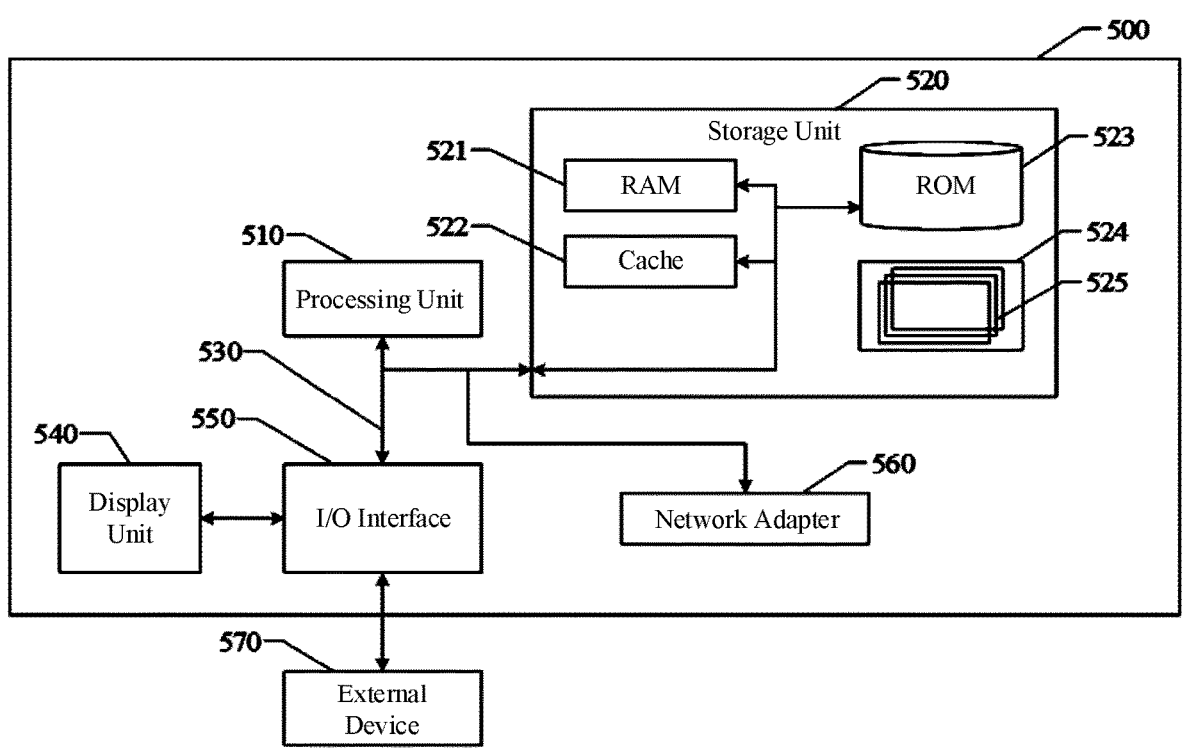
FIG. 5 schematically shows a schematic structural diagram of a computer system suitable for implementing an electronic device according to some embodiments of the disclosure.

As shown in FIG. 5, the electronic device 500 takes a form of a general-purpose computing device. Components of the electronic device 500 may include, but are not limited to, the above at least one processing unit 510, the above at least one storage unit 520, a bus 530 connecting different system components (including the storage unit 520 and the processing unit 510), and a display unit 540.

Wherein the storage unit stores program codes, which may be executed by the processing unit 510, such that the processing unit 510 executes steps of various exemplary embodiments according to the disclosure described in the above "Exemplary Methods" section of the specification.

For example, the processing unit 510 may perform steps as shown in FIG. 4, including: step S410, acquiring training data of a user that is constituted by standard feature values and measurement feature data input multiple times by at least one user, wherein the training data of each user includes a standard feature value set and a measurement feature data set; S420, training a data calculation model of each user by using the training data; S430, acquiring current feature data of a target user, and determining a data calculation model of the target user according to the current feature data and the measurement feature data set; and S440, calculating a user feature value of the target user by using the current feature data and the data calculation model of the target user.

The storage unit 520 may include a readable medium in a form of a volatile storage unit, for example, a random access storage unit (RAM) 521 and/or a cache storage unit 522, and may further include a read only storage unit (ROM) 523.

The storage unit 520 may further include a program/utility 524 having a group of (at least one) program modules 525, and such program modules 525 include, but not limited to: operating systems, one or more application programs, other program modules, and program data. An implementation of a network environment may be included in each or some combination of these examples.

The bus 530 may be representative of one or more of several types of bus structures, including a memory cell bus or memory cell controller, a peripheral bus, a graphics acceleration port, a processing unit, or a local area using any of a plurality of bus structures.

The electronic device 500 may also communicate with one or more external devices 570 (for example, keyboards, pointing devices, Bluetooth devices, etc.), with one or more devices that enable a user to interact with the electronic device 500, and/or with any device (for example, routers, modems, etc.) that enables the electronic device 500 to communicate with one or more other computing devices. Such communication may be performed through input/output (I/O) interface 550. Also, the electronic device 500 may communicate with one or more networks (for example, a local area network (LAN), a wide area network (WAN), and/or a public network such as the Internet) through a network adapter 560. As shown, the network adapter 560 communicates with other modules of electronic device 500 via the bus 530. It should be understood that, although not shown in the drawing, other hardware and/or software modules may be used in conjunction with electronic device 500, including but not limited to: microcodes, device drivers, redundant processing units, external disk drive arrays, RAID systems, tape drives, data backup storage systems, and the like.

From the description of the above embodiments, those skilled in the art may easily understand that the exemplary embodiments described herein may be implemented by software, or may be implemented by software combined with necessary hardware. Therefore, the technical solutions according to the embodiments of the disclosure may be embodied in the form of software products, and the software products may be stored in a non-volatile storage medium (which may be CD-ROM, U disk, mobile hard disk, etc.) or on a network, including several instructions to cause a computing device (which may be a personal computer, a server, a terminal apparatus, a network device, or the like) to execute the method according to the embodiments of the disclosure.

Figure 6:
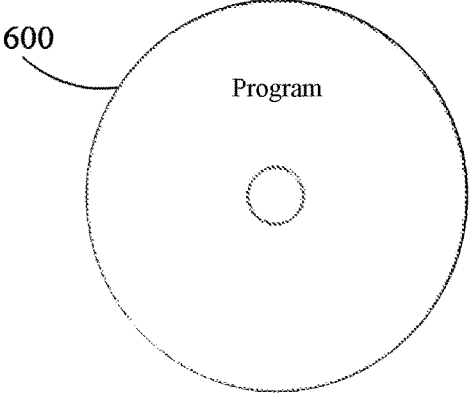
FIG. 6 schematically shows a schematic diagram of a computer-readable storage medium according to some embodiments of the disclosure.

In some embodiments of the disclosure, there is further provided a computer-readable storage medium on which a program product capable of implementing the above methods according to the present specification is stored. In some possible embodiments, various aspects of the disclosure may also be implemented in a form of a program product including program codes, which are configured to cause a terminal device to execute steps of various exemplary embodiments according to the disclosure described in the above "Exemplary Methods" section of the specification, when the program product is run on the terminal device Referring to FIG. 6, a program product 600 for implementing the above methods according to an embodiment of the disclosure is described, which may adopt a portable compact disc read only memory (CD-ROM) and include program codes, and may run on a terminal device, such as a personal computer. However, the program product according to the disclosure is not limited thereto, and in this document, the readable storage medium may be any tangible medium that contains or stores a program that may be used by or in connection with an instruction execution system, apparatus, or device.

The program product may employ any combination of one or more readable medium. The readable medium may be a readable signal medium or a readable storage medium. The readable storage medium may be, for example, but not limited to, an electrical, magnetic, optical, electromagnetic, infrared, or semiconductor system, apparatus or device, or any combination thereof. More specific examples (a non-exhaustive list) of readable storage medium include: an electrical connection with one or more wires, a portable disk, a hard drive, a random access memory (RAM), a read only memory (ROM), an erasable programmable read only memory (EPROM or flash memory), an optical fiber, a portable compact disk read only memory (CD-ROM), an optical storage device, a magnetic storage device, or any suitable combination thereof.

A computer readable signal medium may include a propagated data signal in baseband or as part of a carrier wave with readable program code embodied thereon. Such a propagated data signal may take a variety of forms including, but not limited to, an electromagnetic signal, an optical signal, or any suitable combination of thereof. A readable signal medium may also be any readable medium other than a readable storage medium, and the readable medium may transmit, propagate, or transport a program for use by or in connection with an instruction execution system, apparatus, or device.

Program codes embodied on the readable medium may be transmitted using any suitable medium, including but not limited to wireless or wire lines, optical fiber cables, RFs, etc., or any suitable combination thereof.

Program codes for performing the operations of the disclosure may be written in any combination of one or more programming languages, and the programming languages include object-oriented programming languages such as Java, C++, etc., and further include conventional procedural programming languages such as the "C" language or similar programming languages. The program codes may execute entirely on the user's computing device, partly on the user's device, as a separate software package, partly on the user's computing device and partly on a remote computing device, or entirely on the remote computing device or server execute on. In the case of the remote computing device, the remote computing device may be connected to the user computing device through any kind of network, including a local area network (LAN) or a wide area network (WAN), or may be connected to an external computing device (e.g., using an Internet service provider business via an Internet connection).

In addition, the above drawings are merely schematic illustrations of the processes included in the methods according to the exemplary embodiments of the disclosure, and are not intended to be limiting. It is easy to understand that the processes shown in the above drawings do not indicate or limit the chronological order of these processes. In addition, it is also readily understood that these processes may be performed synchronously or asynchronously, for example, in a plurality of modules.

Other embodiments of the disclosure will readily occur to those skilled in the art upon consideration of the specification and practice of the invention disclosed herein. The disclosure is intended to cover any variations, uses, or adaptations of the disclosure that follow the general principles of the disclosure and include common knowledge or conventional technical means in the technical field which are not disclosed by the disclosure. The specification and embodiments are to be regarded as exemplary only, with the true scope and spirit of the disclosure being indicated by the claims.

It is to be understood that the disclosure is not limited to the precise structures described above and illustrated in the accompanying drawings, and that various modifications and changes may be made without departing from the scope thereof. The scope of the disclosure is limited only by the appended claims.

What is claimed is:

1. A user feature value measurement method, comprising:
   generating training data of at least one user that by acquiring standard feature values and measurement feature data input multiple times by the user, wherein the training data of each user comprises a standard feature value set and a measurement feature data set;
   training a data calculation model of each user based on the training data;
   measuring current feature data of the target user, and calculating correlation coefficients between the current feature data and multiple measurement feature data sets;
   determining a data calculation model corresponding to measurement feature data with a correlation coefficient greater than or equal to a second preset threshold as the data calculation model of the target user; wherein the correlation coefficient is greater than or equal to the second preset threshold, corresponding to the user login being determined; and
   calculating a user feature value of the target user based on the current feature data and the data calculation model of the target user.

2. The method according to claim 1, further comprising:
   acquiring a current standard feature value of the target user when the user feature value is not within a preset range; and
   updating the training data based on the current feature data and the current standard feature value when a difference between the user feature value and the current standard feature value is greater than a preset value.

3. The method according to claim 1, further comprising:
   acquiring a current standard feature value of the target user at a preset time interval; and
   updating the training data based on the current feature data and the current standard feature value when a difference between the user feature value and the current standard feature value is greater than a preset value.

4. The method according to claim 2, wherein the updating the training data based on the current feature data and the current standard feature value comprises:
   determining a target correlation degree as a maximum value of correlation degrees calculated between the current feature data of the target user and a plurality of measurement feature data corresponding to the target user;
   replacing the measurement feature data corresponding to the current feature data by the current feature data when the target correlation degree is greater than or equal to a first preset threshold; and
   replacing the standard feature values corresponding to the current feature data by the current standard feature value.

5. The method according to claim 4, wherein the updating the training data based on the current feature data and the current standard feature value further comprises:
   when the target correlation degree is less than the first preset threshold, adding the current feature data and the current standard feature value to the training data, and deleting a group of standard feature values and measurement feature data firstly input by the target user.

6. The method according to claim 1, wherein the training the data calculation model of the user based on the training data comprises:
   updating parameters in the data calculation model based on the training data.

7. The method according to claim 1, wherein the calculating the correlation coefficients between the current feature data and the multiple measurement feature data sets comprises:
   obtaining a correlation coefficient by calculating an average value of correlation degrees between the current feature data and each measurement feature data in one of the multiple measurement feature data sets; and
   obtaining the correlation coefficients by traversing the multiple measurement feature data sets.

8. A non-transitory computer-readable storage medium on which a computer program is stored, wherein the program, when executed by a processor, is used for implementing a user feature value measurement method comprising:
   generating training data of at least one user that by acquiring standard feature values and measurement feature data input multiple times by the user, wherein the training data of each user comprises a standard feature value set and a measurement feature data set;
   training a data calculation model of each user based on the training data;
   measuring current feature data of the target user, and calculating correlation coefficients between the current feature data and multiple measurement feature data sets;
   determining a data calculation model corresponding to measurement feature data with a correlation coefficient greater than or equal to a second preset threshold as the data calculation model of the target user; wherein the correlation coefficient is greater than or equal to the second preset threshold, corresponding to the user login being determined; and
   calculating a user feature value of the target user based on the current feature data and the data calculation model of the target user.

9. An electronic device, comprising:

one or more processors; and a memory, configured to store one or more programs which, when executed by the one or more processors, cause the one or more processors to:

generate training data of at least one user that by acquiring standard feature values and measurement feature data input multiple times by the user, wherein the training data of each user comprises a standard feature value set and a measurement feature data set;

train a data calculation model of each user based on the training data;

measure current feature data of the target user, and calculate correlation coefficients between the current feature data and multiple measurement feature data sets;

determine a data calculation model corresponding to measurement feature data with a correlation coefficient greater than or equal to a second preset threshold as the data calculation model of the target user; wherein the correlation coefficient is greater than or equal to the second preset threshold, corresponding to the user login being determined; and calculate a user feature value of the target user based on the current feature data and the data calculation model of the target user.

10. The electronic device according to claim 9, wherein the one or more processors are further caused to:

acquire a current standard feature value of the target user when the user feature value is not within a preset range; and update the training data based on the current feature data and the current standard feature value when a difference between the user feature value and the current standard feature value is greater than a preset value.

11. The electronic device according to claim 9, wherein the one or more processors are further caused to:

acquire a current standard feature value of the target user at a preset time interval; and update the training data based on the current feature data and the current standard feature value when a difference between the user feature value and the current standard feature value is greater than a preset value.

12. The electronic device according to claim 10, wherein the one or more processors are further caused to:

determine a target correlation degree as a maximum value of correlation degrees calculated between the current feature data of the target user and a plurality of measurement feature data corresponding to the target user;

replace the measurement feature data corresponding to the current feature data by the current feature data when the target correlation degree is greater than or equal to a first preset threshold; and replace the standard feature values corresponding to the current feature data by the current standard feature value.

13. The electronic device according to claim 12, wherein the one or more processors are further caused to:

when the target correlation degree is less than the first preset threshold, add the current feature data and the current standard feature value to the training data, and delete a group of standard feature values and measurement feature data firstly input by the target user.

14. The electronic device according to claim 9, wherein the one or more processors are further caused to:

update parameters in the data calculation model based on the training data.

15. The electronic device according to claim 9, wherein the one or more processors are further caused to:

obtain a correlation coefficient by calculating an average value of correlation degrees between the current feature data and each measurement feature data in one of the multiple measurement feature data sets; and obtain the correlation coefficients by traversing the multiple measurement feature data sets.

* * * * *